(12) United States Patent
Herrmann

(10) Patent No.: US 9,499,292 B2
(45) Date of Patent: Nov. 22, 2016

(54) METHOD FOR OPERATING A LABELLING MACHINE

(75) Inventor: Jurgen Herrmann, Rosenheim (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 13/817,917

(22) PCT Filed: Aug. 25, 2011

(86) PCT No.: PCT/EP2011/004263
§ 371 (c)(1),
(2), (4) Date: Feb. 20, 2013

(87) PCT Pub. No.: WO2012/031693
PCT Pub. Date: Mar. 15, 2012

(65) Prior Publication Data
US 2013/0146207 A1 Jun. 13, 2013

(30) Foreign Application Priority Data
Sep. 7, 2010 (DE) .................. 10 2010 044 580

(51) Int. Cl.
| | | |
|---|---|---|
| *B32B 41/00* | (2006.01) | |
| *B65C 9/42* | (2006.01) | |
| *B65C 9/40* | (2006.01) | |
| *G01N 21/90* | (2006.01) | |

(52) U.S. Cl.
CPC . *B65C 9/42* (2013.01); *B65C 9/40* (2013.01); *B65C 2009/407* (2013.01); *G01N 21/9045* (2013.01)

(58) Field of Classification Search
CPC ................ B65C 9/045; B65C 9/40; G01N 2021/8841; G11B 21/02; G11B 21/21; G11B 5/6005
USPC .......... 156/64, 350, 351, 360, 378, 379, 567
See application file for complete search history.

(56) References Cited

U.S. PATENT DOCUMENTS

| | | | |
|---|---|---|---|
| 5,735,996 A * | 4/1998 | Asghar et al. | 156/448 |
| 2006/0037706 A1* | 2/2006 | Putzer | 156/360 |
| 2006/0150578 A1 | 7/2006 | Zwilling | |
| 2010/0071830 A1* | 3/2010 | Putzer | 156/64 |
| 2010/0110197 A1* | 5/2010 | Lindner | 348/161 |
| 2010/0141756 A1* | 6/2010 | Grote | B65C 9/067 348/127 |

FOREIGN PATENT DOCUMENTS

| | | |
|---|---|---|
| DE | 44 41 245 A1 | 5/1996 |
| DE | 10 2004 005 994 A1 | 9/2005 |
| DE | 20 2005 017 180 U1 | 1/2006 |
| DE | 10 2004 040 634 A1 | 3/2006 |

(Continued)

*Primary Examiner* — Michael N Orlando
*Assistant Examiner* — Joshel Rivera
(74) *Attorney, Agent, or Firm* — Occhiuti & Rohlicek LLP

(57) ABSTRACT

A method for operating a labelling machine includes, at a first inspection unit, detecting feature coordinates of a design feature of a container, transferring the feature coordinates to a second inspection unit that follows a labelling assembly, and at the second inspection unit, while synchronizing the feature coordinates of the design feature, inspecting the container for correct label seating by tracking the feature coordinates of the design feature along a conveying path from the first inspection unit to said second inspection unit.

19 Claims, 1 Drawing Sheet

(56) References Cited

FOREIGN PATENT DOCUMENTS

| | | |
|---|---|---|
| DE | 20 2005 020 478 U1 | 5/2007 |
| DE | 10 2007 031 218 A1 | 1/2008 |
| DE | 20 2004 021 611 U1 | 6/2009 |
| DE | 10 2008 034 744 A1 | 1/2010 |
| DE | 10 2008 050 249 A1 | 4/2010 |
| DE | 10 2008 051 791 A | 4/2010 |
| EP | 1 627 816 A1 | 2/2006 |

* cited by examiner

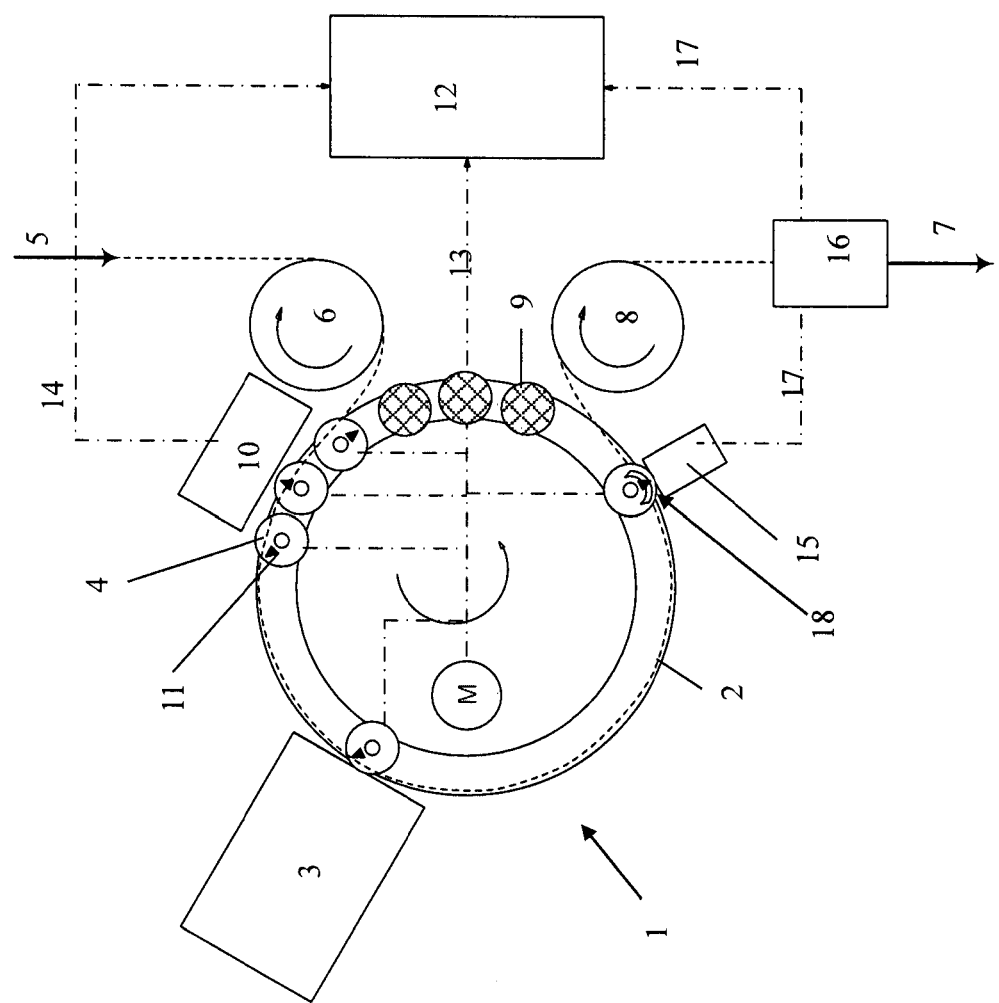

METHOD FOR OPERATING A LABELLING MACHINE

CROSS REFERENCE TO RELATED APPLICATION

This application is the national phase under 35 USC 371 of international application no. PCT/EP2011/004263, filed Aug. 25, 2011, which claims the benefit of the priority date of German application no. 10 2010 044 580.0, filed Sep. 7, 2010. The contents of the aforementioned applications are incorporated herein in their entirety.

FIELD OF DISCLOSURE

The invention relates to a method for operating a labelling machine.

BACKGROUND

Containers to be labelled can, for example, be used as bottles for liquids such as beverages. The containers, e.g. bottles, can consist of a transparent or translucent material, for example glass, or of a translucent plastic, e.g. PET. But it is also conceivable that the containers consist of other materials and can be filled with other content.

Before the containers are supplied to the labelling machine, they are thoroughly inspected with suitable inspection devices. For example, it is envisaged that an inspection for foreign matter be performed in which the containers are inspected for unwanted foreign matter in their interiors. For example using belt conveyors, the containers are supplied to the labelling machine on its infeed side. The labelling machine, for example, has a wheel-like main star or a labelling carousel in which the containers are supplied to a labelling assembly so that the containers are provided with labels. Furthermore, prior to reaching the labelling assembly, the containers are oriented into a target position in which the containers are to be labelled so that the respective labels on the respective containers are always identically oriented. The containers are discharged, on the outfeed side, from the labelling machine or from the labelling carousel, with re-inspections then being carried out. The onward transport to the downstream inspection devices can also be performed by means of transporters or belt conveyors. For example, the containers can be checked for sufficient filling level. In the subsequent inspections, the labels are checked e.g. for correct seating, correct orientation relative to embossings or such design features and/or damages, to name but a few examples of inspections.

It is also known to arrange a first inspection unit as an orientation station and a second inspection unit e.g. as a label seating control at the labelling carousel itself.

DE 20 2005 017 180 U1 relates to a device for orienting containers and a labelling machine with such a device. The containers have at least one geometric container feature (embossing) which is to be twisted into a target position. The containers are pre-oriented with a first camera system. In the transport orientation of the container, there follows a further camera system which effects an orientation into the target position, wherein the further camera system captures a narrower area of the circumferential surface than the first camera system. Thus, DE 20 2005 017 180 U1 proposes a multi-stage, namely a three-stage, orientation for the final fine orientation, for which four cameras are provided. The first two cameras, as seen in the conveying direction, form the first orientation stage, the following third camera serves the further orientation, with the following fourth camera serving the fine orientation.

DE 20 2005 020 478 U1 deals with a label seating control of containers that were labelled on a labelling machine. The label seating control has a camera for imaging the containers equipped with labels. An optical facility is arranged between the camera and the container, said facility generating beam paths that capture labels arranged circumferentially and/or above one another, with distance in between, in a staggered manner. In doing so, only the label surfaces of interest are inspected, with all remaining surface areas of the container being disregarded. In this respect, a correct seating of the label relative to a possible embossing cannot be checked with the label seating control of DE 20 2005 020 478 U1.

DE 10 2004 005 994 A1 discloses a labelling machine. It has a device for supplying labels and a labelling assembly. The labelling assembly has a label container, a glue roller, a rotatable carrier provided with glueable removal segments, and a gripping cylinder. Thus, for example, bottles can be provided with labels, wherein the labelling machine can for example be designed as a rotary runner, a linear machine or even a horizontal runner. In the outfeed area of the labelled bottles, a label seating control facility is arranged with which the desired arrangement of the labels on the bottles is monitored. It is conceivable to check the labels for correct seating, for example relating to design features (so-called embossings) arranged on the bottles. It is also possible to check neck labels and chest labels for correct orientation to one another or also relative to the design features. In case of a change of the label seating outside a specifiable tolerance limit, the label seating control facility conveys corresponding signals for selecting a correction facility which acts upon the labelling assemblies so that a correct label seating can be achieved. Naturally, the bottles provided with an incorrectly oriented label are picked out in a rejection device which, of course, is also possible via the correspondingly generated signal of the label seating control facility.

It is known that the labelled containers are re-oriented in respect of the embossing by means of a detection system downstream of the labelling assembly (DE 10 2008 050 249 A1), to be able to perform, for the label seating control, a seating control regarding a crease-free or damaged seating and also regarding the correct orientation relative to the embossing. For example, bottles or similar containers are filled with content by means of a filling device, to then be supplied to the labelling machine. The containers are oriented (first inspection unit) in the labelling machine or before, for example relating to design features (so-called embossings), so that the labels can be applied to the container in orientation to the design features. The labelled containers are re-oriented after labelling and moved on or transported at a (second) inspection device which can be designed as a label seating control. If the label seating control detects containers with a bad or faulty label seating, a signal for rejection is generated. The rejected containers, for example bottles, are stored on a separate transporter. In this respect, for a re-orientation between the labelling assembly and the label seating control, a further detection system is provided, e.g. with the first inspection unit designed as an orientation station.

DE 10 2007 031 218 A1 deals with a device comprising a turntable which is rotatable relative to a base; drives which are arranged on the turntable, wherein each drive comprises an angle sensor; rotary plates which are arranged on the turntable, wherein each drive drives a rotary plate; and a marking track that is immovably connected with the base and revolves around the turntable. Each drive is allocated a sensor on the turntable, with which the marking track can be read out, wherein each drive comprises an electronic circuit with which the orientation regarding the base of the respective rotary plate driven by the drive can be determined from the signal of the angle sensor of the drive and the signal of the allocated sensor. In the rotary plate drive, a program is deposited in the form of a target motion sequence that specifies which rotation angle the rotary plate is to assume in respect of the base relative to the turntable at the turntable's rotation angle currently detected by the sensor. Depending on the application, a different motion sequence of the rotary plate can thus be implemented in case of a rotation of the turntable.

DE 44 41 245 A1 discloses a method for controlling labelled vessels. The control device is integrated into a labelling machine and has a laser range finder. With the laser range finder, it can be ascertained whether a container is provided with a label or not. During an active measurement interval, the laser beam emitted by the laser range finder first hits the surface of a bottle moving past and measures the bottle's distance from the range finder's fixed housing, which thus forms the constant reference point. As soon as the laser beam hits the surface of the label, there arises a sudden reduction in the currently measured distance corresponding to the thickness of the label and, where applicable, of the glue film between the bottle and the label. This sudden change in distance is detected in an evaluation unit and assessed as a criterion for the presence of a label. Correspondingly, the evaluation unit sends no signal or a good signal to a sorting device. If no label exists on the bottle, no sudden change in distance becomes detectable either, so that the evaluation unit emits an error signal to the sorting device which picks out the corresponding bottle. A main disadvantage of this is that the control facility can only ascertain whether a label exists on the bottle or not. However, it cannot be ascertained whether the label is also correctly oriented, for example relative to design features, or has creases.

DE 20 2004 021 611 U1 assumes combined label seating control facilities in which both a label seating control and a contour detection (embossings) are possible. This requires an incident light illumination for detecting both labels and transmitted images as well as a transmitted light illumination for the contour control, wherein two illumination devices emitting from different directions are used. DE 20 2004 021 611 U1 points out that the use of two illumination facilities regarding the matching of individual lighting level and individual lighting duration is problematic, which is why it is proposed to subject containers, with a single illumination facility and specially designed and adapted optical means, to both transmitted light and incident light. The optical means are for example designed as a flat plate with a bright surface or as a mirror which should be arranged at exactly adapted angles and positions relative to the beam path of the single illumination facility. Thus, labels can be checked not only in respect of crease-free or undamaged seating but, simultaneously, also in respect of the correct orientation relative to the embossing. However, this still requires a facility for detecting the embossing, said facility being combined with the label seating control.

SUMMARY

The invention is thus based on the task of specifying a method for operating a labelling machine, said method enabling an orientation of containers according to embossings prior to labelling wherein, for a label seating control, a statement regarding the label position relative to the position of the embossing of the container concerned is possible without further embossing position detection.

In the method according to the invention, it is expedient that feature coordinates of design features of the container are tracked from the position of the first inspection unit arranged in the conveying direction of the labelling machine along the conveying path of the container to a second inspection unit which, for example, is designed as a label seating control.

The first inspection unit has several successive cameras arranged in the conveying direction of the labelling machine, e.g. CCD cameras. It is advantageous for the feature coordinates of the design feature of the container concerned, which are to be passed to the second inspection unit, to be detected by the last camera as seen in conveying direction. Naturally, the term "camera" is not meant to be limiting. Instead, the term "camera" comprises all suitable image or inspection recording facilities.

A design feature within the meaning of the invention comprises, for example, bottle seams and/or surface markings of the container wall, thus so-called embossings.

The method according to the invention preferably comprises the following steps, wherein only the steps after introducing the container concerned into the labelling machine are looked at. Of course, the labelling machine can for example be designed as a rotary runner, linear machine or even horizontal runner.

In a first step after introducing the container into the labelling machine, the container is transported to the first inspection unit which is designed as an orientation station. The first inspection unit, preferably its last camera as seen in the conveying direction, detects the design feature or its feature coordinates, which, as an equivalent for the position of a carrying element on which the container stands upright, is saved or expediently passed by the control system to the second inspection unit, possibly interconnecting a central control unit.

The container is transported to a labelling station. For this purpose, it is apparent that, prior to entering into the labelling station, no further orientation is required in addition to the first orientation due to the first inspection unit.

The labelling station labels the container.

The (labelled) container is transported away from the labelling station in the direction of the second inspection unit.

In the second inspection unit, while synchronising the saved feature coordinates of the design feature, a label seating control is performed which is why the second inspection unit can also be called a label seating control unit.

It is apparent that, due to the feature coordinates of the design feature which are saved or passed to the second inspection unit, a re-orientation of the container prior to entering into the second inspection unit can be dispensed with.

In the known manner, the carrying element is designed as a carrying plate with allocated drive (so-called variodrive), so that the carrying element is rotatable relative to the conveying direction of the labelling machine.

BRIEF DESCRIPTION OF THE FIGURES

Further advantageous designs of the invention are disclosed in the subclaims and the following FIGURE description. The only FIG. 1 shows a labelling machine according to the invention in a basic representation in which the method according to the invention can be applied.

DETAILED DESCRIPTION

FIG. 1 shows a labelling machine 1 which has a labelling carousel 2. By way of example, only one labelling assembly 3 is arranged at the labelling carousel 2. Naturally, several labelling assemblies can also be provided at the labelling carousel 2. By way of example, the labelling machine 1 is designed as a rotary runner. Naturally, labelling machines designed as linear machines or even as horizontal runners are also possible.

Containers 4 to be labelled are supplied to the labelling carousel 2 on an infeed side (arrow 5) which, by way of example, are transported via an infeed star 6. The labelled containers 4 are rejected on a rejection side (arrow 7) from the labelling carousel 2 by means of a rejection star 8.

The labelling carousel 2 has carrier elements 9 on which one container 4 each stands up. The carrier elements 9 rotate according to the rotation of the labelling carousel 2 together with it; however, they each have a rotary drive so that the upstanding container 4 is rotatable about its centre axis relative to the labelling carousel 2 in or against its rotation direction.

In the conveying direction of the labelling carousel 2, a first inspection unit 10 is downstream of the infeed side 5 or the infeed star 6. The first inspection unit 10 virtually represents an orientation station which can detect design features 11 of the respective container 4. The design features 11 can be a bottle seam or surface markings of the container wall, so-called embossings, which are basically represented as an arrow tip. The first inspection unit 10 has, for example, several cameras such as CCD cameras each recording a circumferential section of the container 4 moving past and thus detecting the actual position of the design feature 11, that is the actual position of the container 4 on the respective carrier element 9. This is essentially known, which is why this is not further elaborated here. By means of the resulting actual data and a comparison with required target data, a control signal is generated in a central control unit 12, said signal effecting a transfer of the container 4 from its actual position to its target position by correspondingly twisting the carrier element 9. This is achieved by selecting the carrier element 9 or its drive with the control signal. In this target position, the container 4 is oriented with its particular design feature 11 such that a label 18 can be applied oriented relative to the design feature(s) 11 onto the container 4. In the only FIG. 1, the label 18 only is, by way of example, a chest label, wherein a label within the meaning of the invention can also have a neck label or is applied to the container 4 as an imprint.

The central control unit 12 is connected in the known manner, via control wires 13, with the respective carrier element 9 or its drive and, via a control wire 14, connected with the first inspection unit so that a data exchange or the generated signal is directly implemented. The control wires 13 and 14 are shown dot-dashed, with a wireless data exchange between the components also being possible.

If the respective container 4 reaches the labelling assembly 3, an adapted change in position of the design feature 11 is effected in order to apply the label or other identifications such as imprints crease-free and undamaged and oriented relative to the design features 11. In this respect, the term "labelling" within the meaning of the invention means the application of identifications such as labels and/or imprinting or the like on the corresponding outer periphery of the container 4.

After labelling, the labelled container 4 is supplied to a second inspection unit 15 in which the labels are checked, for example, for correct seating relative to the design feature 11 but, for example, also for crease-free and undamaged seating. Both inspection tasks are performed with adapted, different illumination methods. If the second inspection unit 15, for example, detects a label that is applied with creases or damaged, a corresponding control signal to a rejection device 16 is generated, which effects the rejection of the faulty container 4. The rejection device 16 is connected with the second inspection unit 15 via a control wire 17, wherein the control wire 17 continues onto the central control unit 12. The control wire 17 is also shown dot-dashed, with a wireless data exchange also being conceivable. Thus, to date, the second inspection unit 15 not only checks the correct seating of the label as regards crease-free or undamaged seating but also the correct orientation relative to the design feature 11.

This is where the invention applies, beginning with the first inspection unit 10 so that, in the second inspection unit 15, only the correct seating of the label in respect of crease-free and/or undamaged seating is checked unconnected with the oriented position of the design feature 11 relative to the label.

It is expedient for one of the cameras of the first inspection unit 10, preferably the last camera of the first inspection unit 10 as seen in the rotation direction of the labelling carousel 2, to transmit feature coordinates of the design feature(s) 11 via the control wire 14 to the central control unit 12 or to the second inspection unit 15 so that it tracks feature coordinates or the position of the carrying element 9 on the conveying path of the container 4 from the first inspection unit 10 past the labelling assembly 3 to the second inspection unit, i.e. pursues the track of the particular container 4 concerned regarding each resulting twisting of the container 4 or its design features 11 from the target position recorded with the last camera. These tracked feature coordinates of the container 4 or of the carrier element 9 concerned, which can also be called a rotating plate with variodrive, are passed to or saved in the second inspection unit 15 which can also be called a label seating control. Thus, a re-detection of the container 4 concerned or a position detection of the embossing by means of further cameras before the labelling assembly 3 and in particular before the second inspection unit 15 is no longer required.

Moreover, with the procedure according to the invention, an additional detection of the design feature 11 by means of label seating control can be dispensed with, with only creases, damages or such distortions having to be detected. This is advantageous in respect of a very simple design of the second inspection unit 15 or the label seating control, as it now only has to be designed for the clear 360° all-round processing of the container 4 or of the label, wherein standard light sources and standard illumination methods can be used. Specific illuminations for detecting design features are no longer required, so that the label seating control can be standardised throughout.

It is expedient for the invention that the feature coordinates of the embossing of the container 4, thus for example of a bottle on the labelling carousel 2 or labelling star, are tracked from the position of the last (orientation) camera in the rotation direction of the labelling carousel 2 to the camera unit of the second inspection unit.

Thus, in a first step, the design feature 11 of the container 4 is detected and, as an equivalent for the position of the carrying element 9 (angle degree/angle position of the variodrive) or of the container 4, saved or transferred by the control system.

The container 4 is, rotatingly, transported to the labelling station 3, or rotated (rotation of the labelling carousel 2).

The container 4 is labelled at the labelling station 3.

The (labelled) container 4 is transported away from the labelling station 3 in the direction of the second inspection unit 15 or to the label seating control, or rotated (rotation of the labelling carousel 2).

In the second inspection unit 15 or in the label seating control, while synchronising with the saved embossing position, only one further label seating control is performed. An additional detection of the embossing by means of label seating control is dispensed with due to the procedure according to the invention. For this, the feature coordinates of the embossing are simply accepted by the second inspection unit 15 from the last orientation camera.

Naturally, the rotation directions of the labelling carousel 2, shown in FIG. 1, are only examples in connection with the infeed and rejection stars 6 and 8. It must be pointed out that labelling machines have a considerable throughput of containers so that, naturally, not only a single carrier element 9 but several carrier elements 9 are provided on which a container 4 each stands upright.

REFERENCE LIST 1 labelling machine
2 labelling carousel
3 labelling assembly
4 container
5 infeed side
6 infeed star
7 rejection side
8 rejection star
9 carrying element
10 first inspection unit
11 design feature
12 central control unit
13 control wire
14 control wire
15 second inspection unit
16 rejection device
17 control wire
18 label

The invention claimed is:

1. A method for operating a labeling machine, said method comprising, at a first inspection unit, detecting feature coordinates of a design feature of a container, wherein said feature coordinates are indicative of a position of said design feature, wherein said design feature is a member of a class that includes bottle seams, surface markings of a container wall, and embossing on said container wall, transferring data representative of said feature coordinates to a second inspection unit that follows a labeling assembly, at said second inspection unit, receiving said data from said first inspection unit, at said second inspection unit, storing said data, at said second inspection unit, while synchronizing said feature coordinates of said design feature, inspecting said container for correct label seating by tracking said feature coordinates of said design feature along a conveying path from said first inspection unit to said second inspection unit, labeling said container in said labeling assembly, transporting said container from said labeling assembly to said second inspection unit, without performing a detection of said design feature, and at said second inspection unit, inspecting placement of said label based at least in part on said data received from said first inspection unit and stored in said second inspection unit.

2. The method of claim 1, wherein said first inspection unit comprises several cameras that are successively arranged in a conveying direction, said method further comprising transferring said feature coordinates of said design feature from a last camera encountered along said conveying direction to said second inspection unit, whereby the total number of cameras in a combination that consists of the first and second inspection units is greater than two.

3. The method of claim 1, further comprising, after introducing said container into said labeling machine, supplying said container to said first inspection unit, wherein said first inspection unit is configured as an orientation unit, wherein said first inspection unit has first camera and a last camera, wherein said last camera is encountered by said container during progression of said container along a conveying direction after said container has already encountered said first camera, wherein said method further comprises, using said last camera to detect said feature coordinates of said design feature, and wherein said method further comprises saving said feature coordinates as an equivalent for position of a carrying element.

4. The method of claim 1, further comprising transporting said container from said first inspection unit toward said labeling assembly, and, using a signal provided by said first inspection unit, causing orientation of said container before entry thereof into said labeling assembly.

5. The method of claim 1, further comprising, after introducing said container into said labeling machine, supplying said container to said first inspection unit, said first inspection unit being configured as an orientation unit having a last camera encountered during progression of a container along a conveying direction, using said last camera, detecting said feature coordinates of said design feature, and transmitting said feature coordinates to said second inspection unit.

6. The method of claim 1, wherein detecting feature coordinates of a design feature comprises detecting feature coordinates of a seam on a container wall of the container.

7. The method of claim 1, wherein detecting feature coordinates of a design feature comprises detecting feature coordinates of an embossing on a container wall of the container.

8. The method of claim 1, wherein detecting feature coordinates of a design feature comprises detecting feature coordinates of a surface marking on a container wall of the container.

9. The method of claim 1, wherein inspecting placement of said label based at least in part on data from said first inspection unit comprises determining position of a label relative to said design feature based in part on said feature coordinates provided by said first inspection unit.

10. A method for operating a labeling machine, said method comprising, at a first inspection unit, detecting feature coordinates of a design feature of a container, transferring said feature coordinates to a second inspection unit that follows a labeling assembly, at said second inspection unit, while synchronizing said feature coordinates of said design feature, inspecting said container for correct label seating by tracking said feature coordinates of said design feature along a conveying path from said first inspection unit to said second inspection unit, labeling said container in said labeling assembly, transporting said container from said labeling assembly to said second inspection unit, without performing a detection of said design feature, and at said second inspection unit, inspecting placement of said label based at least in part on data received from said first inspection unit and stored in said second inspection unit.

11. A method for operating a labeling machine, wherein feature coordinates of a design feature of a container are detected by a first inspection unit and are transferred to a second inspection unit downstream of a labeling device, wherein the inspection of the container in the second inspection unit, with regard to the correct label location, is carried out by comparison of the feature coordinates of the design feature of the container concerned, these coordinates being detected by the first inspection unit and stored in the second inspection unit, and with the feature coordinates of the design feature being tracked along the conveying path from the first inspection unit to the second inspection unit.

12. The method of claim 11, wherein the first inspection unit comprises a plurality of cameras, which are arranged sequentially to one another in the conveying direction, wherein the feature coordinates of the design feature are transferred from a first camera, seen in the conveying direction, to the second inspection unit.

13. The method of claim 11, further comprising a first step after the introduction of the container into the labeling machine, in which the container is conveyed to the first inspection unit in the embodiment of an alignment station, of which the last camera seen in the conveying direction detects the feature coordinates of the design feature and stores them as equivalent for a position of a carrier element or, respectively transfers them by control technology methods to the second inspection unit.

14. The method of claim 11, further comprising conveying the container from the first inspection unit to the labeling device, wherein the container is adequately aligned before introduction into the labeling device by means of the first inspection unit.

15. The method of claim 11, further comprising the labeling of the container in the labeling device and conveying the container from the labeling device to the second inspection unit without a detection of the design feature being carried out.

16. A method comprising operating a labeling machine that has first inspection unit, a labeling assembly, and second inspection unit, wherein the labeling assembly is between the first inspection unit and a second inspection unit, wherein operating said labeling machine comprises causing a container to traverse a conveying path that extends from said first inspection unit, past said labeling assembly, to said second inspection unit, causing said first inspection unit to detect information indicative of a design feature of a container, causing data representative of said feature coordinates to be transferred from said first inspection unit to said second inspection unit, causing said second inspection unit to receive said data representative of said feature coordinates from said first inspection unit, causing said data representative of said feature coordinates to be stored at said second inspection unit, at said second inspection unit, tracking said feature coordinates of said design feature as said container traverses said conveying path from said first inspection unit to said second inspection unit, labeling said container in said labeling assembly, transporting said container from said labeling assembly to said second inspection unit, without performing a detection of said design feature, and at said second inspection unit, inspecting placement of said label based at least in part on said data received from said first inspection unit and stored in said second inspection unit.

17. The method of claim 16, wherein said design feature is a bottle seam.

18. The method of claim 13, further comprising twisting said carrier element.

19. The method of claim 1, wherein said first inspection unit comprises two cameras that are successively arranged in a conveying direction, said method further comprising transferring said feature coordinates of said design feature from a last camera encountered along said conveying direction to said second inspection unit.

* * * * *